United States Patent
Arai et al.

(10) Patent No.: US 6,365,899 B1
(45) Date of Patent: Apr. 2, 2002

(54) PROCESS FOR DETERMINATION OF BLACKENING OF A LAMP

(75) Inventors: Tetsuji Arai, Yokohama; Shinji Suzuki, Kawasaki; Yoshiki Mimura, Yokohama, all of (JP)

(73) Assignee: Ushiodenki Kabushiki Kaisha, Tokyo (JP)

(*) Notice: Subject to any disclaimer, the term of this patent is extended or adjusted under 35 U.S.C. 154(b) by 0 days.

(21) Appl. No.: 09/452,387

(22) Filed: Dec. 1, 1999

(30) Foreign Application Priority Data

Dec. 1, 1998 (JP) .......................................... 10-341293

(51) Int. Cl.$^7$ ................................................. G01J 5/00
(52) U.S. Cl. ................................ 250/338.1; 250/341.5; 250/343
(58) Field of Search ............................ 250/338.1, 340, 250/341.5, 343, 339.13

(56) References Cited

U.S. PATENT DOCUMENTS

| | | | |
|---|---|---|---|
| 4,252,443 A | * 2/1981 | Lucas et al. | ........... 250/559.04 |
| 4,271,358 A | * 6/1981 | Schwarz | ................. 250/338.1 |
| 5,399,856 A | * 3/1995 | Sandridge et al. | ....... 250/252.1 |

FOREIGN PATENT DOCUMENTS

| | | | |
|---|---|---|---|
| EP | 1 006 553 A1 | * 6/2000 | ............. 250/338.1 |
| GB | 2 094 471 | 9/1982 | |
| WO | WO 91/02237 | 2/1991 | |

OTHER PUBLICATIONS

Patent Abstracts of Japan, vol. 017, No. 214 (E–1357), Apr. 27, 1993, & JP 04 351832 A (Matsushita Electric Works Ltd), Dec. 7, 1992, English Abstract.

* cited by examiner

*Primary Examiner*—Huy Mai
(74) *Attorney, Agent, or Firm*—Nixon Peabody LLP.; David S. Safran (57) ABSTRACT

A process for determination of blackening of a lamp in which the blackening of a lamp can be determined without visual inspection in real time or during operation is achieved by the spectral radiant energy which is emitted by the lamp bulb being measured and evaluated based on the difference that exists between when blackening occurs as compared to when blackening does not occur. Therefore, blackening of a lamp can be determined by determining the change of the spectral radiant energy emitted by the bulb. Furthermore, in a lamp in which the bulb temperature changes, the spectral radiant energy emitted by the bulb can be measured at two different wavelengths and blackening of the lamp can be determined based on the change of the ratio relative to each other.

6 Claims, 5 Drawing Sheets

PROCESS FOR DETERMINATION OF BLACKENING OF A LAMP

BACKGROUND OF THE INVENTION

1. Field of the Invention

For layer formation, diffusion, baking and the like of a semiconductor wafer (hereinafter called a "wafer"), a heat treatment device of the light irradiation type is used, in which the article to be treated is rapidly heated, held at a high temperature, and quickly cooled. As a light source for this purpose, a filament lamp is used. Furthermore, for semiconductor lithography, for curing, drying of ink and adhesive, and for similar purposes a discharge lamp, such as a super-high pressure mercury lamp, high pressure mercury lamp, or the like is used. The present invention relates to a process for determination of blackening of a lamp in which the blackening of a lamp, such as the above described filament lamp, discharge lamp, and the like can be determined without visual inspection.

2. Description of Related Art

Heat treatment of the light irradiation type in the production of semiconductors is performed in broad areas, such as layer formation, diffusion, baking and the like.

In each of these treatments, a wafer is heated to a high temperature. If a heat treatment device of the light irradiation type is used for the heat treatment, the wafer can be quickly heated. The temperature of the wafer can be increased to at least 1000° C. in a time frame of between a few seconds and a few dozen seconds. Furthermore, rapid cooling can be achieved when the light irradiation stops.

Figure 10:
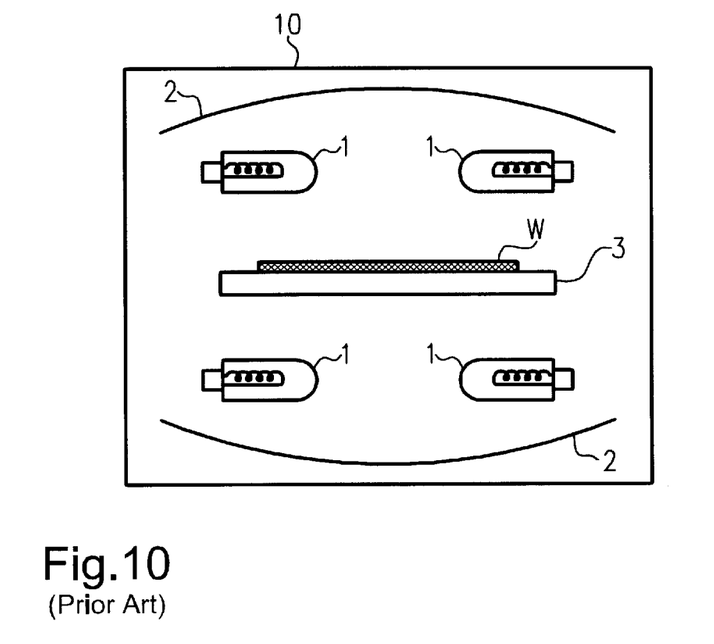
FIG. 10 shows an example of a known heat treatment device of the light irradiation type.

FIG. 10 is a schematic representation of an example of the above described heat treatment device of the light irradiation type. In the figure, a heat treatment device 10 of the light irradiation type comprises several filament lamps 1 for heat treatment and mirrors 2. To subject a workpiece W to heat treatment, the workpiece W, for example, a wafer or the like, is placed on a holder 3 of ceramic or the like, and then, in a treatment chamber in which the above described filament lamps 1 and mirrors 2 are located. By operating the filament lamps 1, the article to be treated is irradiated with the light emitted by the filament lamps 1 and is rapidly heated.

If, when heating the wafer by the above described heat treatment device 10 of the light irradiation type, nonuniformity of the temperature distribution in the wafer occurs, a phenomenon arises in the wafer which is called "slip" and which means dislocation faults. Here, the danger is that scrap will be produced.

Therefore, when a wafer is being heat treated using a heat treatment device of the light irradiation type, there is a need to control the amount of light irradiation in order to make the temperature distribution of the wafer uniform.

For the light source of the heat treatment device of the light irradiation type, lamps are used which have a filament and which emit IR radiation with high efficiency, as is shown in FIG. 10. When these filament lamps are used over a long time, the material contained in the filament, for example, tungsten, gradually vaporizes, and it is deposited on the wall surface of the inside of the lamp bulb. The locations at which this vapor deposition has occurred are colored black; this is called "blackening."

When blackening occurs in a lamp, the location at which the blackening has occurred no longer transmits the light from the filament. On the surface irradiated with light, directly below the blackened location, the irradiance and the temperature of the surface irradiated with light are reduced.

As a result, there are cases in which in the wafer nonuniformity of the temperature distribution arises, and thus, scrap is formed.

During lamp operation, the blackened location more easily absorbs heat energy from the filament. In the state in which blackening is there, if lamp operation continues, the temperature rises until a temperature is reached at which the silica glass of the lamp bulb (of the glass vessel of the lamp, which is hereinafter called "bulb" or "bulb glass") softens, by which the bulb is deformed and breaks. Therefore, there is a need for premature replacement of the lamp in which blackening has occurred with a new lamp.

Even in the above described discharge lamp which is used for semiconductor lithography, for curing, drying of ink and adhesive, and for similar purposes, the irradiance on the surface which has been irradiated with light likewise drops when blackening occurs. There are cases in which scrap is produced.

Conventionally, blackening of a lamp is visually determined. That is, in a regular examination, irradiation is stopped, the photoheating chamber and the lamp housing are opened, the state of the lamps in the light source part is visually inspected, and in the presence of blackening, the affected lamps are replaced.

In the above described heat treatment device of the light irradiation type, the lamps are located in a photoheating chamber or in a lamp housing and cannot be examined from the outside. When blackening occurs between two regular inspections in the lamps, therefore, it cannot be determined.

Therefore, there are cases in which blackening of the lamps reduces the irradiance and produces scrap, as was described above, or in which the lamps are heated and therefore damaged.

To eliminate the above described defects, there is a demand for determining the blackening of a lamp in real time or in a state in which the heat treatment device of the light irradiation type is in operation. However, conventionally, there has been no process for determining the blackening of a lamp in real time or during operation.

SUMMARY OF THE INVENTION

The invention was devised to eliminate the above described defects. Therefore, a first object of the invention is to devise a process for determining blackening of a lamp without visual inspection in real time or during operation.

A second object of the invention is to devise a process for determining blackening of a lamp in which the blackening of the lamp bulb can be determined regardless of the temperature of the lamp bulb in real time or during operation.

A solid emits spectral radiant energy which corresponds to the respective temperature and which is characteristic for the respective solid according to the principle of solid state emission. This spectral radiant energy emitted by the lamp bulb at the time at which the lamp is not blackened differs from the spectral radiation energy at the time at which the lamp is blackened. Thus, the blackening of a lamp can be determined without visual inspection by determining the change of the spectral radiant energy emitted by the lamp bulb.

The spectral radiant energy also changes with the temperature of a body. In a lamp in which the input power supplied to the lamp and the temperature of the lamp bulb change, there are, therefore, also cases in which, when a change of the radiant energy emitted by the bulb occurs at a single defined wavelength, it cannot be distinguished whether this change was caused by the blackening or by the change of the temperature of the lamp bulb.

In one such case, the radiant energy emitted by the lamp bulb at two different wavelengths (in two different wavelength ranges) is measured and the ratio to one another is determined. This ratio is compared to the value in the case in which no blackening has occurred in the lamp. When the amount of change is greater than or equal to a stipulated value, this means that blackening has occurred in the lamp. In this way, the blackening of a lamp can be determined without visual inspection, even if the temperature of the lamp bulb changes.

In the case of a filament lamp, during lamp operation, the emission part emits an enormous amount of spectral radiant energy. Therefore, there are cases in which the spectral radiant energy emitted by the bulb compared to the energy emitted by the emission part drops into the background and can be perceived only as a background noise level. When, after turning off the lamp and before the bulb cools, the spectral radiant energy is measured, the blackening of a lamp can be determined without the spectral radiant energy emitted by the emission part exerting an effect.

In a discharge lamp there are, furthermore, cases in which the spectral radiant energy distribution in the emission part exhibits peaks. In this case, the blackening of a lamp can be determined without the influence of the spectral radiant energy emitted by the emission part, when the wavelength range in which the spectral radiant energy emitted by the bulb is measured, while avoiding the wavelengths emitted by the lamp emission part with maximum intensity, is chosen such that in this measurement wavelength range the spectral radiant energy emitted by the emission part with respect to the spectral radiant energy emitted by the bulb can be called background noise level and does not disrupt measurement of the energy emitted by the lamp bulb.

The objects are achieved as follows in accordance with the invention:

(1) The radiant energy emitted by the lamp bulb is measured at a stipulated wavelength (in a stipulated wavelength range). This measured value is compared to the measured value at the start of lamp use. When the amount of increase is greater than or equal to a predetermined value, it is assumed that the blackening has occurred in the lamp.

(2) The radiant energy emitted by the lamp bulb is measured at two different wavelengths (in two different wavelength ranges) and the ratio to one another is determined. This ratio is compared to the value in the case in which no blackening has occurred in the lamp. When the amount of change is greater than or equal to a predetermined value, this means that blackening has occurred in the lamp.

(3) In (1) and (2), the radiant energy emitted by the lamp bulb is measured after the lamp is turned off and before the lamp cools.

(4) In (1) and (2), wavelengths are chosen in a region in which the radiant energy emitted by the lamp emission part as compared to the radiant energy emitted by the bulb is somewhat lower. Thus, essentially the radiant energy emitted by the lamp bulb is measured.

In the following, the invention is specifically described using several embodiments which are shown in the drawings.

DETAILED DESCRIPTION OF THE INVENTION

In the following, preferred embodiments of the invention are described with reference to a filament lamp which is used as the light source for a heat treatment device of the light irradiation type. However, the invention is not limited to the above described filament lamp, and can also be used for a super-high pressure mercury lamp, high pressure mercury lamp, or the like, as was described above.

(1) Embodiment 1

Determination of the blackening of a lamp by the difference of the spectral radiant energy when blackening occurs and the spectral radiant energy when blackening does not occur In a filament lamp which is provided with a filament and which is used as the light source of a heat treatment device of the light irradiation type, there is a device for cooling the lamp and for cooling the device so that the bulb temperature of the lamp during operation reaches roughly 800° C. by supplying the nominal wattage (1073 K).

According to the principle of solid state emission, a solid emits a spectral radiant energy which is dependent on temperature and which is characteristic of the solid. The spectral radiant energy is a function of the temperature and the wavelength.

Figure 1:
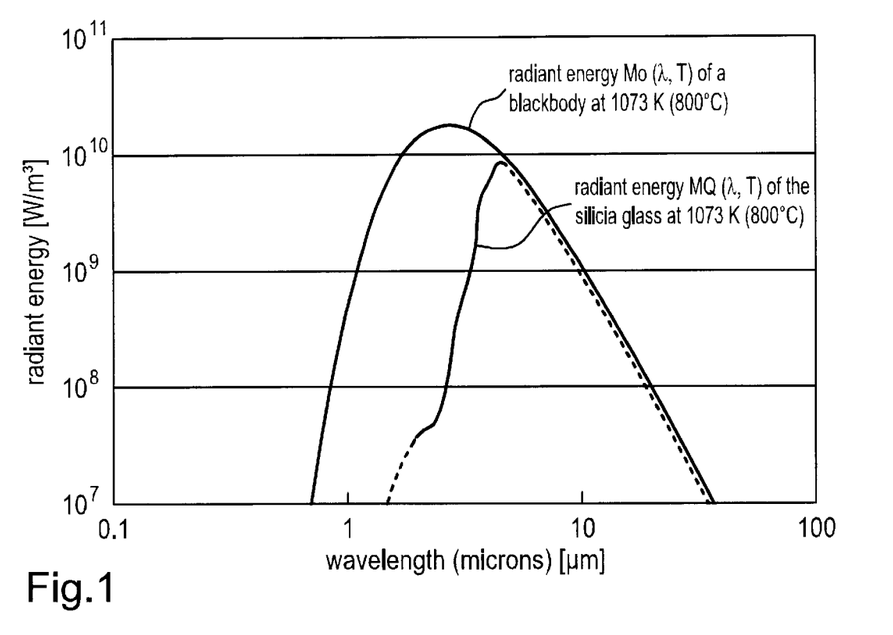
FIG. 1 is a graph depicting the spectral radiant energy of a blackbody and the spectral radiant energy of the glass which is used for the bulb of a filament lamp at 800° C.
Figure 2:
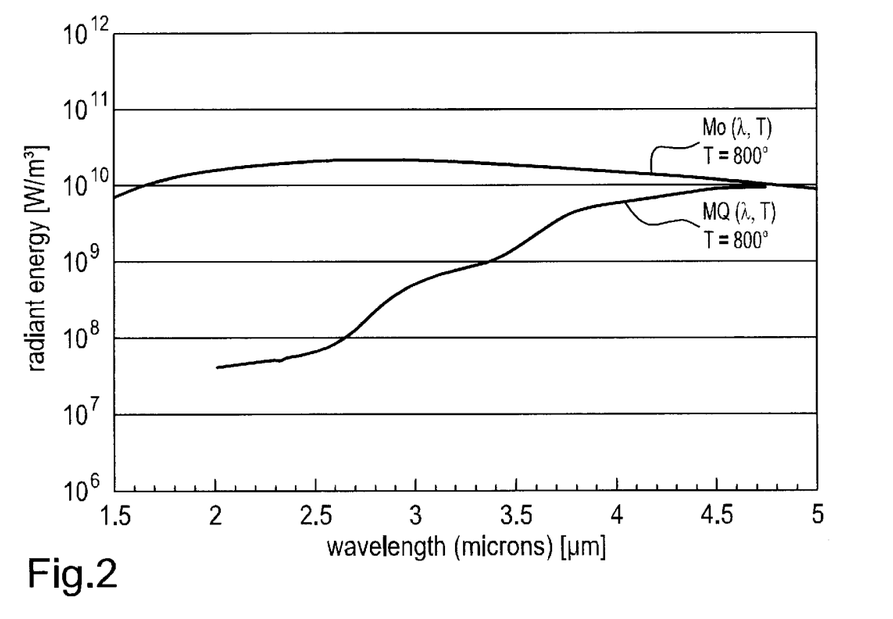
FIG. 2 in an enlarge view of the wavelength range around 1.5 to 5 microns in the curves plotted in FIG. 1.

FIG. 1 shows the spectral radiant energy Mo ($\lambda$,T) of a blackbody and the spectral radiant energy MQ ($\lambda$, T) of the glass which is used for the bulb of the filament lamp at 800° C. (1073 K). Here, the x-axis plots the wavelength (microns) and the y-axis plots the radiant energy (W/m$^3$). FIG. 2, furthermore, is an enlarged view of the wavelength range around 1.5 to 5 microns of FIG. 1.

The spectral radiant energy (MQ ($\lambda$, T)) of the bulb glass can be computed by multiplying the spectral radiant energy (Mo ($\lambda$, T) of blackbody radiation by the spectral emissivity $\epsilon$ ($\lambda$, T)) for the respective wavelength component of the bulb glass (with respect to the spectral emissivity of the glass, for example, reference is made to "Special emissivity and absorption coefficient of silica glass at extremely high temperatures in the semitransparent," Infrared Physics, Vol. 19, pp. 465–469, Pergammon Press Ltd, 1979).

Here, a case of operation of the lamp at 800° C. (1073 K) is assumed.

As was described above, the spectral radiant energy MQ ($\lambda$, T) in FIGS. 1 & 2 is emitted by the bulb glass.

On the other hand, also the substance vaporized onto the inside wall of the bulb glass emits spectral radiant energy at 800° C. (1073 K) when at this temperature blackening has occurred in the lamp bulb.

The spectral radiant energy (Mn'($\lambda$, T)) of the vaporized substance which is observed from outside the lamp is computed by multiplying the spectral radiant energy (Mn ($\lambda$, T)) of the vaporized substance by the transmission factor (I$\lambda$/Io$\lambda$) at the respective wavelength of the bulb glass at this temperature because it passes through the bulb glass.

Figures 3A, 3B:
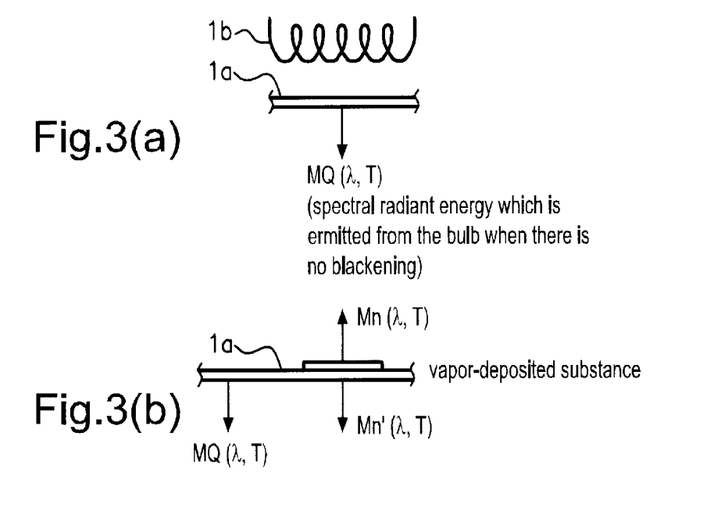
FIGS. 3(a) & 3(b) schematically depict the spectral radiant energy emitted by the lamp bulb, respectively, when blackening does not occur and when blackening does occur.

As is shown, in FIG. 3(*a*), the spectral radiant energy emitted by the bulb glass 1*a* of the lamp when blackening of the lamp does not occur is labeled Mo ($\lambda$, T), while that emitted when blackening of the lamp does occur is labeled MQ ($\lambda$, T)+Mn'($\lambda$A, T) (FIG. 3(*b*)).

Therefore, the spectral radiant energy emitted by the bulb when blackening does occur differs from that when blackening does not occur. Accordingly, the blackening of the lamp can be determined by determining this change of the spectral radiant energy.

Figure 4:
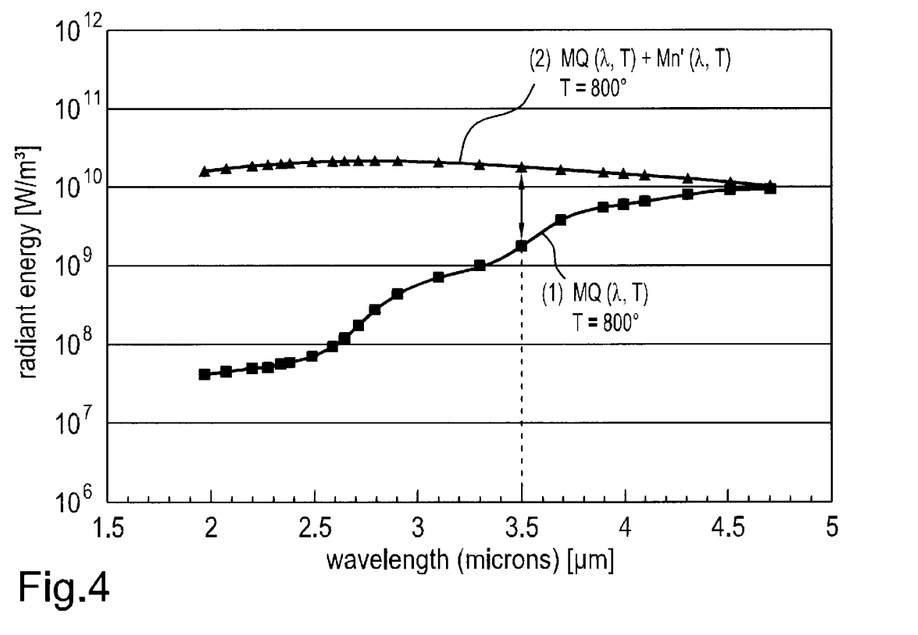
FIG. 4 is a graph depicting the spectral radiant energy which is emitted by the bulb glass in the same wavelength range as in FIG. 2 and at 800° C. (1073 K)

FIG. 4 shows a schematic of the spectral radiant energy which is emitted by the bulb glass in the same wavelength range as in FIG. 2 and at 800° C. (1073 K). In the figure, (1) represents the spectral radiant energy (MQ ($\lambda$, T)) when blackening does not occur and (2) represents the spectral radiant energy (MQ ($\lambda$, T)+Mn'($\lambda$, T)) when blackening does occur.

Here, the spectral radiant energy Mn'($\lambda$, T) of the vaporized substance which has passed through the bulb glass is determined as follows:

Tungsten, which is used for the lamp filament, was chosen as the vaporizing substance which causes blackening. By multiplying the spectral radiant energy Mo ($\lambda$, T) of the blackbody radiation with the spectral emissrity of tungsten and the transmission factor of the bulb glass at the aforementioned wavelengths, the spectral radiant energy was determined. The thickness of the bulb glass was 1 mm.

As FIG. 4 shows, especially in a wavelength range of less than or equal to 3.5 microns, the spectral radiant energy emitted by the bulb is increased by at least one power of ten when the case of blackening of the bulb is compared to the case of absence of blackening. Therefore, the blackening of a lamp can be determined by determining the spectral radiant energy using a detector with which the spectral radiant energy can be measured in this wavelength range.

The specific measurement is described below:
(1) An actual measurement of the radiant energy emitted by the bulb of a new lamp without blackening and of the radiant energy emitted by the bulb of a blackened lamp is taken. The wavelength at which the values of the spectral radiant energies which have been determined for both cases exceed the ranges of measurement error and background noise and change to a large extent is called the measurement wavelength at which the spectral radiant energy is measured.
(2) A detector is prepared with which, at the wavelength which has been established in the above described manner, the spectral radiant energy can be determined. In practice, a bandpass filter is located in front of the detector, and the spectral radiant energy is measured in a certain wavelength range which contains the measurement wavelength.
(3) A new (unused) lamp is placed in the device, it is operated and the spectral radiant energy emitted by the bulb is measured in doing so, i.e., in the state of absence of blackening.
(4) A blackened lamp is placed in the device, it is operated and the spectral radiant energy emitted by the bulb is measured in doing so.
(5) A reference value is established by the two measured values in a suitable manner and this reference value is used to assess what amount of change of the measured value is called occurrence of blackening. In this way, preparation for the measurement is ended.
(6) During operation of the device, the spectral radiant energy emitted by the lamp bulb is always measured by the above described detector in real time. When the determined value exceeds the reference value, the result is obtained that blackening has been ascertained. Therefore, the lamp is then replaced.

Figure 5:
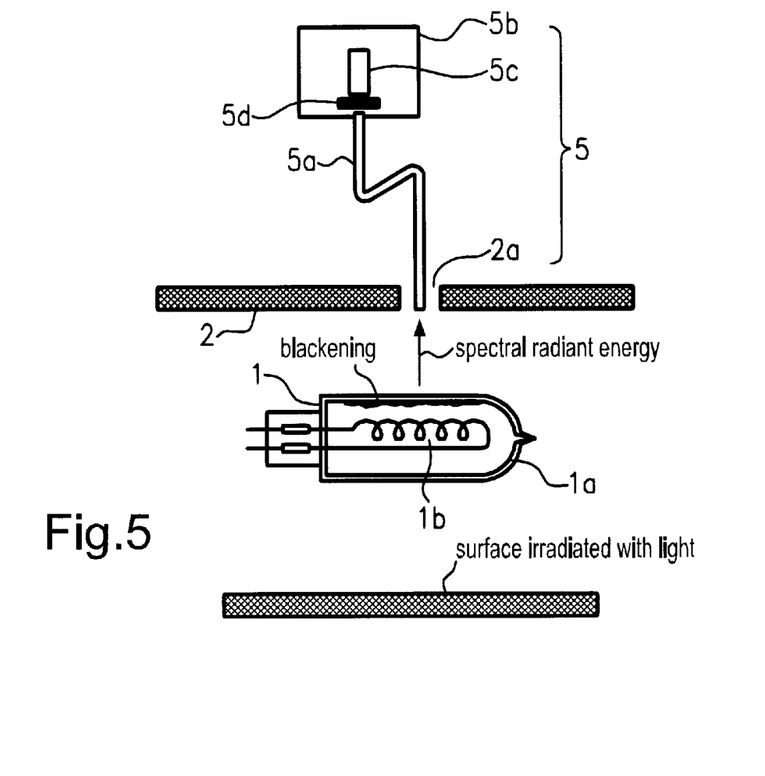
FIG. 5 schematically depicts the arrangement of an embodiment of a measurement system for determining the blackening of a filament lamp.

FIG. 5 shows a schematic of the arrangement of an embodiment of a measurement system for determining the blackening of a filament lamp which is used as the light source of the above described heat treatment device of the light irradiation type.

Figure 6:
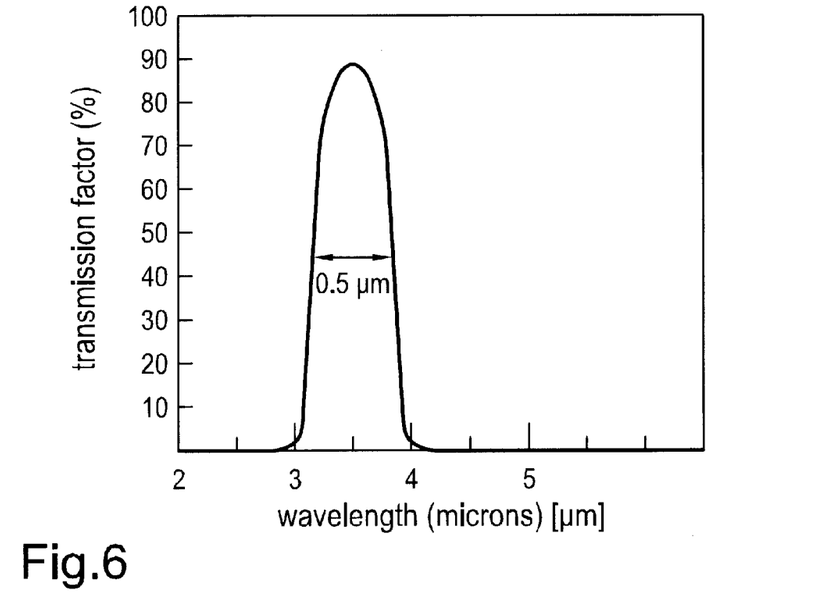
FIG. 6 is a graph showing one example of the wavelength characteristic of a bandpass filter.

In the FIG. 5, a lamp 1 has a bulb 1*a* and a filament 1*b*, and a mirror 2 is provided with a through opening 2*a*. The spectral radiant energy emitted by the lamp 1 is sent via an optical fiber 5*a*, which is located in the through opening 2*a*, to a main part 5*b* of a detector 5 for spectral radiant energy. In the main part 5*b*, there are a determination element 5*c* for measuring the spectral radiant energy and a bandpass filter 5*d*. The bandpass filter 5*d* is used to supply spectral radiant energy to the determination element 5*c* only in the wavelength range to be measured, as was described above. FIG. 6 shows an example of the wavelength characteristic of the bandpass filter 5*d*.

Since the radiant energy of the blackbody and the radiant energy of the fused silica have the wavelength characteristic which is shown in FIG. 1, it is desirable to use a bandpass filter 5*d* with a full width at half maximum (FWHM) of roughly 0.5 microns as shown in FIG. 6.

For example, a radiation thermometer can be used as the means for measuring the spectral radiant energy. Since a radiation thermometer can acquire the spectral radiant energy of a blackbody in a stipulated wavelength range, blackening can thus be determined.

FIG. 5 shows an example for measurement of the spectral radiant energy of a single lamp. In a device provided with several lamps, however, there are several detectors 5 for the spectral radiant energy in a number set according to the number of lamps.

Thus, the blackening of the respective lamp can be determined in real time and without visual inspection by taking the above described measurements (1) to (6) using the measurement system with the above described arrangement. Thus, the lamps can be replaced when blackening occurs in them.

In the case of a filament lamp, during lamp operation the emission part, i.e., the filament, emits an enormous amount of spectral radiant energy. The spectral radiant energy emitted by the filament through the bulb is designated Mn'($\lambda$, T). On this basis, there are cases in which the spectral radiant energy emitted by the bulb MQ ($\lambda$, T) or MQ ($\lambda$, T)+Mn'($\lambda$, T) drops to simple background noise.

In this case, the lamp can be turned off and the spectral radiant energy emitted by the bulb can be measured.

Since the filament has low heat capacity, when turned off it is immediately cooled, while the bulb which is made of glass is not as easily cooled due to its high heat capacity. Therefore, it can be appreciated that, for a while after the lamp is turned off, the bulb continues to emit spectral radiant energy to the same degree as in operation. This time interval is used to take the measurement.

Figure 7:
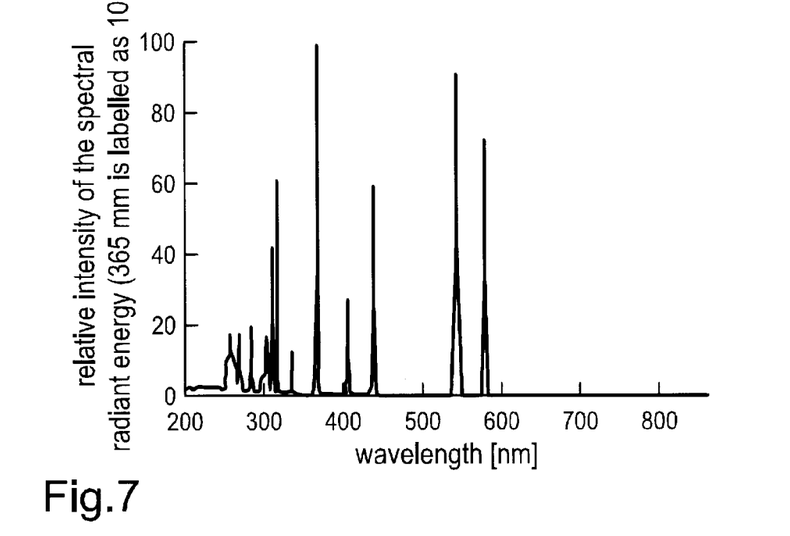
FIG. 7 is a graph depicting one example of the spectral radiant energy distribution of the emission part of a discharge lamp.

In a discharge lamp, there are cases (see FIG. 7) in which the spectral radiant energy of the emission part has spectral lines of great intensity. In the case in which the spectral radiant energy distribution of the emission part has spectral lines of great intensity, the spectral radiant energy emitted by the bulb even during lamp operation in which the emission part emits a large amount of spectral radiant energy can be measured by choosing a wavelength range (outside the wavelengths of the spectral lines of high intensity) in which the spectral radiant energy emitted by the emission part can be labeled background noise with reference to the spectral radiant energy emitted by the bulb.

(2) Embodiment 2

Determination of the blackening of a lamp by comparison of the ratio of the radiant energy which is measured at two different wavelengths (in two different wavelength ranges)

Figure 8:
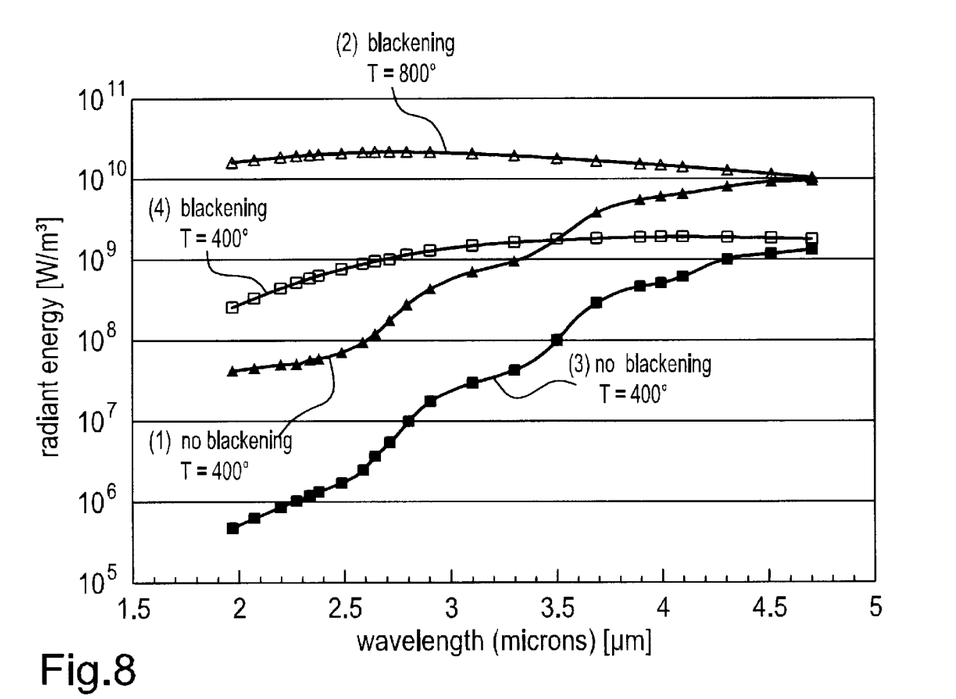
FIG. 8 is a graph which shows, in addition to the curves of FIG. 4, also curves representing the spectral radiant energy emitted by the bulb at 400° C. when blackening occurs and when blackening does not occur.

When only the change of the emission energy at a single certain wavelength (in a single certain wavelength range) is measured, as was described above in (1), it is necessary to watch the following:

The spectral radiant energy changes depending on the temperature of the body according to Planck'sLaw. FIG. 8 is a schematic in which, in addition to the curves of FIG. 4 (which represent the spectral radiant energy which is emitted by the bulb at 800° C.), also the spectral radiant energy is shown which is emitted by the bulb at 400° C. (623 K) when blackening occurs and when blackening does not occur.

Here, (3) is a case of no blackening at 400° C. (623 K) and (4) is a case of blackening at 400° C. (623 K). The respective spectral radiant energy was determined in the same sequence as in FIG. 4.

For the radiant energy emitted by the bulb, e.g., with a wavelength of 3.5 microns, the value when blackening occurs in the bulb glass of the lamp at 400° C. agrees with the value at 800° C. in the state in which the lamp bulb is not blackened.

In particular, in a heat treatment device of the light irradiation type, the amount of light irradiation is always controlled by changing the input power supplied to the lamp, such that the temperature distribution of the wafer at a stipulated temperature is made uniform. By changing the input power supplied to the lamp, the lamp bulb temperature also changes.

Therefore, there are cases in which, when a change of the radiant energy emitted by the bulb occurs at a single defined wavelength, it cannot be distinguished whether this change was caused by the blackening or by the change of the temperature of the lamp bulb.

In the above described device in which the lamp bulb temperature changes, there are cases in which determination of the blackening is difficult.

In this case, blackening of a lamp is determined by separately determining the change of the spectral radiant energy from the lamp bulb by blackening and the change of the spectral radiant energy by the change of bulb temperature, as is described below.

The radiant energy emitted by the lamp bulb is measured at two different wavelengths (in two different wavelength ranges) and the ratio to one another is determined which is compared to the value when blackening of the lamp does not occur. When the amount of change is greater than or equal to a stipulated value, it is ascertained that blackening has occurred in the lamp. The lamps are therefore replaced.

As is apparent from FIG. 8, the amount of emitted spectral radiant energy changes when the temperature changes.

The slope of the plots of the radiant energy emitted by the bulb in the case of no blackening (i.e., the ratio of the radiant energy emitted by the bulb at two different wavelengths) ((1) and (3) in FIG. 8) and the slope of the plots of the radiant energy emitted by the bulb in the case of blackening (i.e., the ratio of the radiant energy emitted by the bulb at two different wavelengths) ((2) and (4) in FIG. 8) however hardly change.

Therefore, by determining the slope of the plots, blackening can be determined regardless of the temperature of the lamp bulb.

In the case of a lamp with the property shown in FIG. 8, for example, the blackening can be determined as follows.

At a wavelength ($\lambda 2$) at which, even when blackening occurs, the amount of radiant energy emitted by the bulb hardly changes, and at a wavelength ($\lambda 1$) at which, when blackening occurs, the amount of radiant energy changes greatly, the radiant energy emitted by the bulb MQ ($\lambda 1$,T) MQ ($\lambda 2$,T) is measured and the ratio to one another MQ ($\lambda 1$,T)/MQ ($\lambda 2$,T) is computed. For example, the radiant energy emitted by the bulb at a wavelength of 3.5 microns and the radiant energy emitted by the bulb at a wavelength of 2.5 microns are measured.

FIG. 8 shows that the radiant energy emitted by the bulb at 400° C. in the case of no blackening at a wavelength of 3.5 microns is roughly $1 \times 10^8$ W/m$^3$ and at a wavelength of 2.5 microns is roughly $2 \times 10^6$ W/m$^3$. The ratio is $1 \times 10^8 / 2 \times 10^6 = 50$.

In the case of blackening at a wavelength of 3.5 microns, the radiant energy emitted is roughly $1.6 \times 10^9$ W/m$^3$ and at a wavelength of 2.5 microns it is roughly $7.5 \times 10^8$ W/m$^3$. Therefore, the ratio is computed in the same way and is 2.1.

On the other hand, as at 800° C., in the case of no blackening, at a wavelength of 3.5 microns, the radiant energy emitted is roughly $1.6 \times 10^9$ W/m$^3$ and at a wavelength of 2.5 microns it is roughly $6.5 \times 10^7$ W/m$^3$. The ratio is 24.6.

In the case of blackening, at a wavelength of 3.5 microns, the radiant energy emitted is roughly $1.6 \times 10^{10}$ W/m$^3$ and at a wavelength of 2.5 microns is roughly $1.8 \times 10^{10}$ W/m$^3$. The ratio is 0.9.

The ratio of the spectral radiant energy at a wavelength of 3.5 microns to the spectral radiant energy at a wavelength of 2.5 microns is shown below using Table 1.

TABLE 1

[spectral radiant energy at a wavelength of 3.5 microns]/[spectral radiant energy at a wavelength of 2.5 microns]

|  | 400° C. | 800° C. |
|---|---|---|
| No blackening | 50 | 24.6 |
| Blackened | 2.1 | 0.9 |

The change of the ratio of the radiant energy emitted by the bulb when blackening occurs changes compared to the change of the ratio of radiant energy as a result of the temperature change by a power of ten. Therefore, in this case, it can be ascertained that blackening has occurred when, for example, a 10-fold change with respect to the ratio in a new lamp has occurred.

As was described above, by measuring the change of the ratio of the radiant energy emitted by the bulb at two suitable wavelengths blackening can be determined without relying on the temperature change of the lamp.

Figure 9:
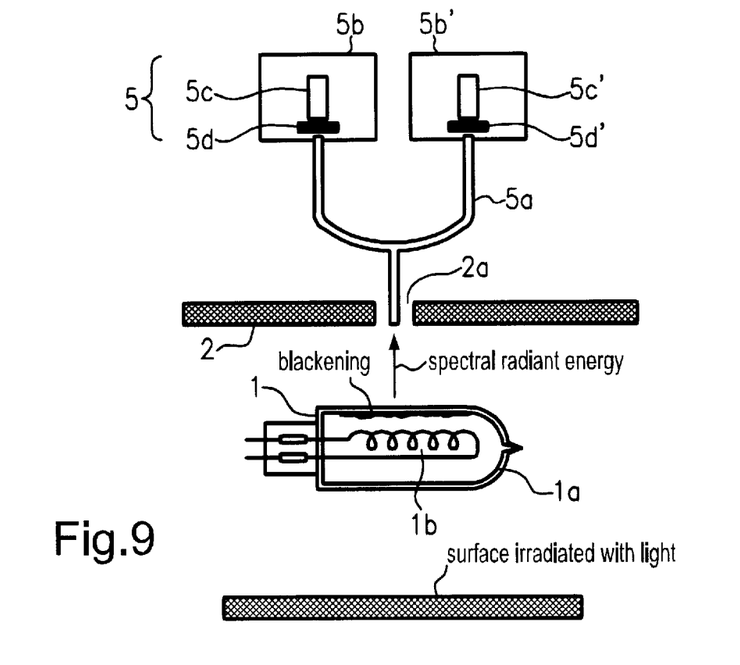
FIG. 9 is a schematic of the arrangement of an embodiment of a measurement system for measuring the spectral radiant energy in two wavelength ranges.

The measurement system for measuring the spectral radiant energy in two different wavelength ranges and for determining blackening of the lamp can be the same as in FIG. 5. In this embodiment, as is shown in FIG. 9, in the detector 5 for the spectral radiant energy, there are a first main part 5b and a second main part 5b', and the spectral radiant energy emitted by the lamp 1 is supplied to the first main part 5b and the second main part 56' via a branched optical fiber 5a.

In the first main part 5b, there is a first bandpass filter 5d which has a wavelength characteristic which transmits only the spectral radiant energy of the first wavelength (in the first wavelength range) λ1. In the second main part 5b', there is a second bandpass filter 5d' which has a wavelength characteristic which transmits only the spectral radiant energy of the second wavelength (in the second wavelength range) λ2. The light transmitted by the first bandpass filter 5d and the second bandpass filter 5d' is incident in the first determination element 5c and a second determination element 5c'.

The two wavelengths (wavelength ranges) λ1, λ2 which are measured by the above described detector 5 are established as follows:

The spectral radiant energy of bulbs of a new lamp without blackening is measured while the lamp temperature changes. Furthermore, the spectral radiant energy of a blackened lamp bulb is measured as the lamp temperature changes. An area is determined and established in which the ratio of the radiant energy at two different wavelengths for blackening differs greatly from that for the absence of blackening.

For example, if one of the wavebands is established as the range (for example, with wavelengths of greater than or equal to 4.5 microns in FIG. 8) in which the radiant energy hardly changes regardless of the presence or absence of blackening, and the other of the wavebands is established as the range (for example, with wavelengths of less than or equal to 3.5 microns in FIG. 8) in which the radiant energy changes greatly due to the presence or absence of blackening, the slope of the curve of the spectral radiant energy changes greatly due to the presence or absence of blackening. This measure is therefore advantageous. Furthermore, numerical values are established in a suitable manner, with which the change of the energy ratio is identified with blackening. In this way, preparation for measurement is ended.

During operation of the device, the measurement system with the above described arrangement measures the spectral radiant energy of an article to be measured using the above described detector at two stipulated wavelengths. Furthermore, the ratio of the measured spectral radiant energy is always determined in real time by a division element or the like. Formation of blackening can be determined by comparison of the ascertained ratio to the ratio in the new lamp.

With respect to the timing of the measurement, it can be taken after the lamp is turned off, when measurement of the spectral radiant energy emitted by the bulb is difficult during lamp operation, as in embodiment 1.

When the spectral radiant energy distribution of the emission part has spectral lines of great intensity, as in a discharge lamp, the wavelengths emitted by the lamp emission part with strong radiation can be avoided and two wavelength ranges can be chosen in which the spectral radiant energy is less than the spectral radiant energy emitted by the bulb. In this way, even during lamp operation, the spectral radiant energy emitted by the bulb can be measured.

Action of the Invention

As was described above, as in accordance with the invention, the following effects can be obtained.

(1) By measuring the change of the spectral radiant energy emitted by the bulb, blackening of the lamp is determined. Thus, the blackening of the lamp can be determined in real time or in a similar state without visual inspection. For example, in the process of rapid heat treatment of a workpiece with a lamp, the blackening of the lamp can be rapidly determined.

Therefore, scrap as a result of a reduction in the irradiance of the lamp can be minimized.

(2) Blackening is determined by measuring the ratio of the spectral radiant energy emitted by the bulb into two different wavelength ranges. In this way, the blackening of the lamp can be determined without relying on the temperature change of the lamp.

(3) By measuring the spectral radiant energy emitted by the bulb after the lamp is turned off, the spectral radiant energy emitted by the bulb can be measured and blackening can be determined, even if measurement of the spectral radiant energy emitted by the bulb is difficult during lamp operation as a result of the spectral radiant energy emitted by the lamp emission part.

(4) When the lamp emission part emits spectral radiant energy at certain wavelengths with high intensity, even during lamp operation, the spectral radiant energy emitted by the bulb can be measured when a wavelength range (outside of the wavelengths with high radiation intensity) is chosen in which the spectral radiant energy emitted by the emission part with respect to the spectral radiant energy emitted by the bulb an be designated the background noise.

What we claim is:

1. Process for determining blackening of a lamp, comprising the following process steps:

measuring radiant energy emitted by a lamp bulb at a predetermined wavelength;

determining an amount of increase of the radiant energy emitted by the bulb and measured after use of the lamp begins with respect to radiant energy measured when the lamp was first turned on; and determining whether blackening of the lamp has occurred on the basis of the amount of increase determined in the preceding step.

2. Process for determination of the blackening of a lamp as claimed in claim 1, wherein the radiant energy is measured after the lamp is turned off.

3. Process for determination of the blackening of a lamp as claimed in claim 1, wherein the radiant energy emitted by the lamp bulb is measured at a wavelength in a range in which the radiant energy emitted by an emission part of the lamp is somewhat lower as compared to the radiant energy emitted by the bulb.

4. Process for determination of the blackening of a lamp, comprising the following process steps:

measuring radiant energy emitted by the lamp bulb at two different wavelengths;

determining a ratio of the radiant energy measured at said two wavelengths relative to each other;

determining an amount of change of the ratio which was determined after use of the lamp begins with respect to the ratio measured when the lamp was first turned on; and determining whether blackening of the lamp has occurred based on the amount of change determined in the preceding step.

5. Process for determination of the blackening of a lamp as claimed in claim 4, wherein the radiant energy is measured after the lamp is turned off.

6. Process for determination of the blackening of a lamp as claimed in claim 4, wherein the radiant energy emitted by the lamp bulb is measured at a wavelength in a range in which the radiant energy emitted by an emission part of the lamp is somewhat lower as compared to the radiant energy emitted by the bulb.

* * * * *